United States Patent [19]

Hancock et al.

[11] Patent Number: 4,840,615
[45] Date of Patent: Jun. 20, 1989

[54] SELF-SEALING INJECTION RESERVOIR

[75] Inventors: John C. Hancock; William R. Dubrul, both of Santa Barbara; Charles J. Heyler, III, Thousand Oaks, all of Calif.

[73] Assignee: McGhan Medical Corporation, Santa Barbara, Calif.

[21] Appl. No.: 167,409

[22] Filed: Mar. 14, 1988

Related U.S. Application Data

[62] Division of Ser. No. 781,965, Sep. 30, 1985, Pat. No. 4,738,657.

[51] Int. Cl.$^4$ .................. A61M 25/00; A61B 19/00
[52] U.S. Cl. ................................ 604/93; 604/244; 128/899; 623/8
[58] Field of Search .............. 128/899; 604/175, 8–10; 623/8

[56] References Cited
U.S. PATENT DOCUMENTS 4,190,040 2/1980 Schulte ............................. 128/899
4,543,088 9/1985 Bootman et al. ............... 604/175 X
4,557,724 12/1985 Gregonis et al. ................ 604/93 X
4,685,447 8/1987 Iversen et al. ...................... 623/8 X Primary Examiner—Stephen C. Pellegrino
Attorney, Agent, or Firm—Klein & Szekeres

[57] ABSTRACT

An injection reservoir or button is adapted for implantation beneath the skin of human and animal patients in conjuction with tissue expanders and drug delivery devices. The injection reservoir includes a base and an exterior wall which define a chamber of liquid reservoir. A duct connects the chamber with an expandable bag of the tissue expander. An elastic rubber member is affixed within the interior of the chamber to act as a sealing member. The rubber member is an inverted dome and is self-sealing to needle punctures because it has a concave interior side which is under compression as a result of having been manufactured into a substantially dome-shaped configuration and thereafter inverted. A metal guard plate is included within the interior of the chamber to guard the base against accidental puncture by an over extended hypodermic needle.

9 Claims, 3 Drawing Sheets

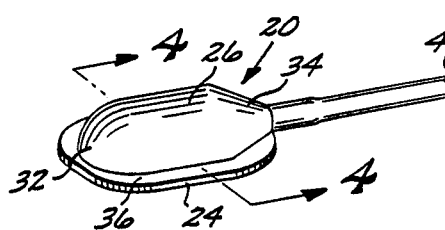
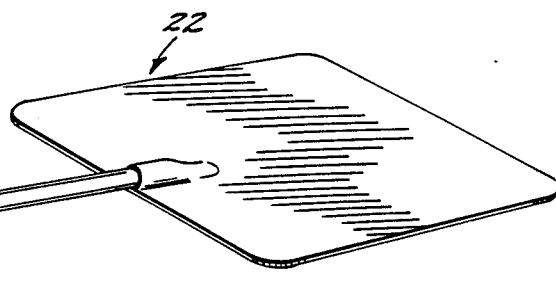
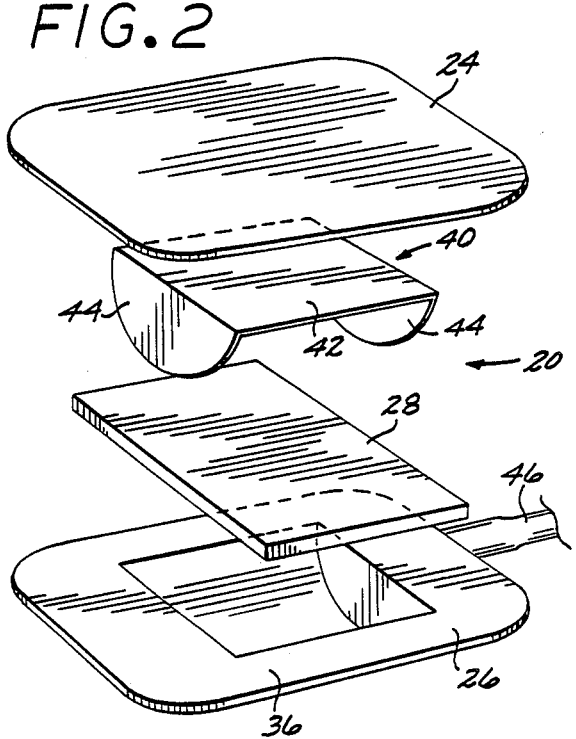
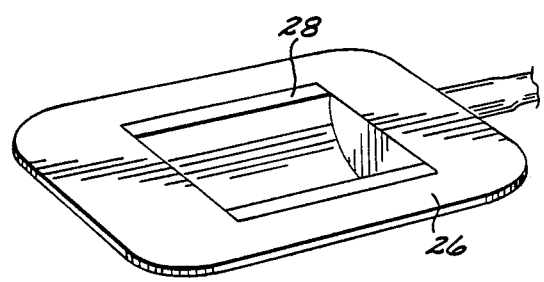
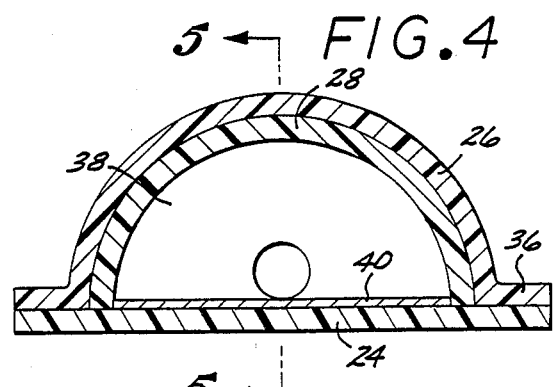
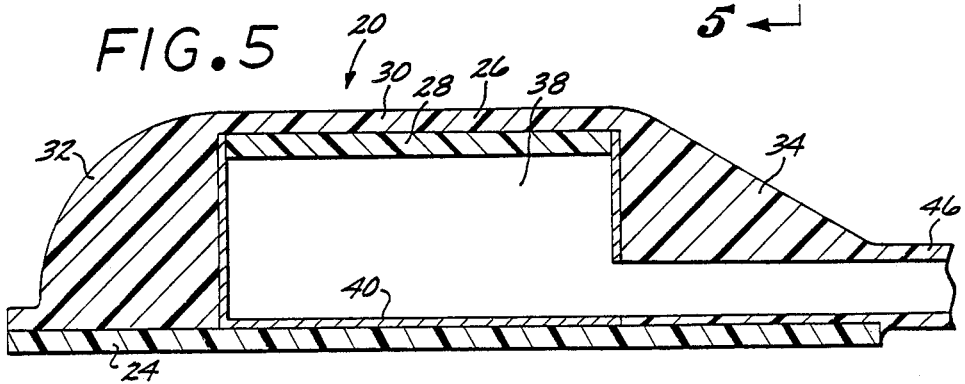

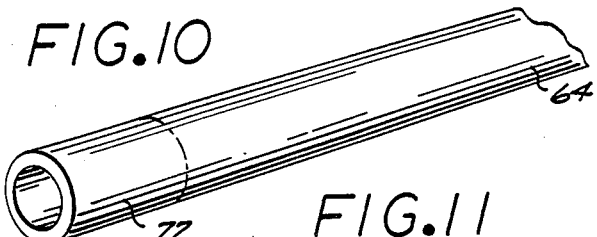
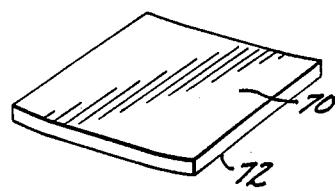
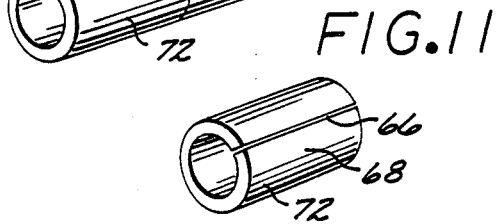
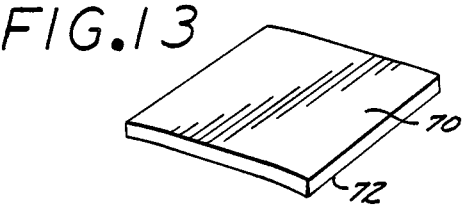
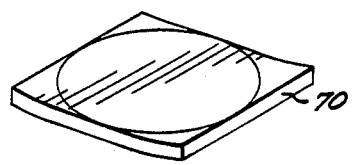
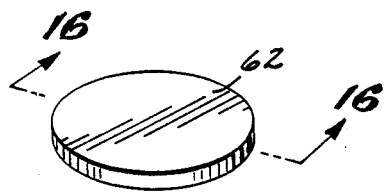
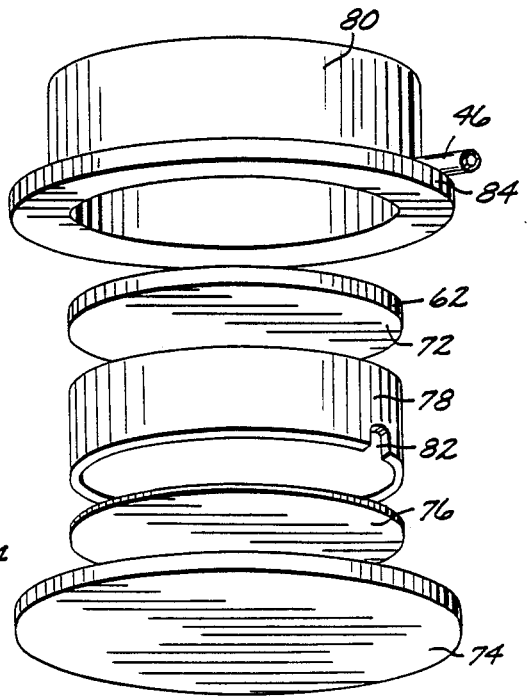
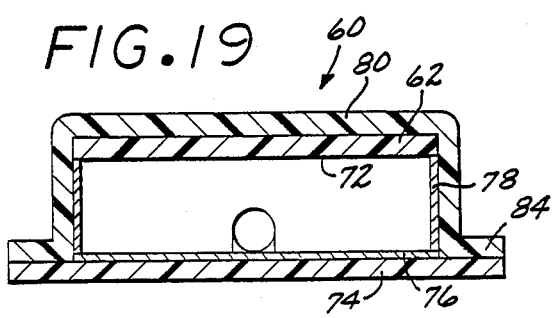

SELF-SEALING INJECTION RESERVOIR

CROSS-REFERENCE TO RELATED APPLICATION

The present application is a divisional of application Ser. No. 781,865, filed on Sept. 30, 1985, now be issued as a U.S. Pat. No. 4,738,657.

BACKGROUND OF THE INVENTION

1. Field of the Invention

The present invention is directed to an injection reservoir which is self-sealing to punctures by a hypodermic needle. More particularly, the present invention is directed to a self-sealing injection reservoir of the type which is implanted under the skin of humans and domestic animals in connection with tissue expanders and various drug delivery systems.

2. Brief Description of the Prior Art

The prior art is well aware of tissue expanding devices which are temporarily implanted under the skin of humans and domestic animals, and which are gradually inflated by injection of saline or similar liquids for the purpose of causing the growth of a skin flap or enlargement. For a detailed description of such tissue expanders, reference is made to U.S. Pat. No. 4,217,889. Briefly summarized, such tissue expanders comprise a surgically implantable bag into which the liquid is introduced to gradually enlarge the bag and thereby to cause the desired skin enlargement or flap formation. After the skin flap has formed, the bag is surgically removed. The skin flap is either used, after severance, for purposes of plastic surgery in other parts of the body, or accommodates a permanent implantation directly beneath the flap. Neither the manner of using the skin flap, nor the permanent implants, form part of the present invention.

For medically self-evident reasons the temporarily implantable tissue expander bag must not leak, and must not be punctured to form a leak, when, from time to time, additional liquid is introduced into the bag. In some situations, liquid must even be withdrawn from the bag without causing a leak. Such addition or withdrawal of liquid is accomplished, in accordance with standard practice in the art, through a substantially non-expandable bioimplantable injection button or reservoir, which is self-sealing to punctures by a hypodermic needle. The self-sealing, non-expandable injection button or reservoir is usually connected to the bag, through a suitable bioimplantable duct or narrow tubing. In some tissue expanders, the injection reservoir is incorporated in the wall of the bag. In other words, to gradually inflate the tissue expander bag liquid is introduced into the bag through a distinct, non-expandable but self-sealing injection reservoir, which is temporarily implanted beneath the skin together with the tissue expander bag.

Injection buttons or reservoirs of the prior art are described in U.S. Pat. Nos. 4,190,040 and 4,428,364.

More particularly, the injection reservoir of U.S. Pat. No. 4,190,040 includes a substantially flat base and a generally dome-shaped, double-walled upper portion, which, together with the base, forms an enclosure or reservoir chamber for the injected liquid. The enclosure is connected to the tissue expander bag with a suitable tubing or duct. The self-sealing capability of the double-walled upper portion is attained by a silicone gel sealant layer which is contained between the two walls. In order to protect the base from puncture by accidentally overextending the hypoderminc needle into the base, a non-puncturable plate member is contained within the enclosure to cover the base.

The injection reservoir of U.S. Pat. No. 4,428,364, on the other hand, is contained within the tissue expander bag itself. In this device, a generally dome-shaped wall of the reservoir has multiple layers of fabric reinforced silicone rubber sheets, with the weave of the fabric in the several layers being oriented in multiple directions. A swelling agent is present in the dome-shaped wall. The forces created by the swelling of the silicone rubber sheets and the restraining force of the fabric cause a compressive stress in the wall, which, in turn, renders the wall self-sealing to punctures by a hypodermic needle.

Although the above-described self-sealing injection buttons or reservoirs function, by-and-large, adequately, improvements are needed, particularly from the standpoint of ease and cost of manufacturing and resistance to leakage. The present invention provides such an improvement.

SUMMARY OF THE INVENTION

It is an object of the present invention to provide a surgically implantable injection button or reservoir which is usable in conjunction with temporarily implanted tissue expander or drug delivery devices, and which is self-sealing to punctures by a hypodermic needle.

It is another object of the present invention to provide a surgically implantable injection button or reservoir which is usable in conjunction with temporarily implanted tissue expander and drug delivery devices, and which is well protected against decapacitating puncture by an accidentally overextended hypodermic needle.

It is still another object of the present invention to provide the injection button or reservoir which meets the above-noted objectives, and whichis relatively economical to manufacture.

The foregoing and other objects and advantages are attained by an injection button or reservoir having a body, including a base, which defines a chamber for holding liquid, and wherein a wall of the chamber is a sheet of resilient elastic rubber disposed in a curvilinear bent configuration in the location where a hypodermic needle is used to puncture the reservoir for the purpose of injecting or withdrawing liquid therefrom. The sheet of resilient elastic rubber is bent into its curvilinear configuration from a substantially flat sheet, so that the interior of the bent sheet is in compression and thereby provides self-sealing capability. In the preferred embodiments, the bent sheet comprises only an inner wall of the injection reservoir, the outer wall being a single molded rubber piece which is affixed to a substantially flat base. A metal guard plate is disposed within the interior of the chamber to guard the base against puncture by an accidentally overextended hypodermic needle.

In another embodiment of the invention, a wall of the chamber of the injection reservoir is self-sealing because it is in compression, comprising a substantially dome-shaped member which has been inverted after molding.

In still another embodiment, the wall of the chamber of the injection reservoir is self-sealing because it is derived from a wall of a cylindrical tubing which has been cut into a substantially flat disc, and inverted so that its interior is in compression.

The objects and features of the present invention are further set forth in the appended claims. The present invention may be best understood by reference to the following description, taken in connection with the accompanying drawings.

BRIEF DESCRIPTION OF THE DRAWINGS

FIG. 1 is a perspective view of a first preferred embodiment of the injection reservoir of the present invention, the figure also showing a tissue expander bag to which the injection reservoir is fluidly connected;

FIG. 2 is an exploded perspective view of the first preferred embodiment of the injection reservoir of the present invention;

FIG. 3 is a perspective view of a top part of the first preferred embodiment of the injection reservoir of the present invention;

FIG. 4 is a cross-sectional view taken on lines 4,4 of FIG. 1;

FIG. 5 is a cross-sectional view taken on lines 5,5 of FIG. 4;

FIG. 10 is a perspective view of a tubing comprising resilient rubber material from which a sealing plate or sheet of a third preferred embodiment of the injection reservoir of the present invention is fabricated;

FIG. 11 is a perspective view of an intermediate in the process of fabricating the sealing plate of the third preferred embodiment;

FIG. 12 is a perspective view of intermediate in the process of fabricating the sealing plate of the third preferred embodiment;

FIG. 13 is a perspective view of still another intermediate in the process of fabricating the sealing plate of the third preferred embodiment;

FIG. 14 is a perspective view of yet another intermediate in the process of fabricating the sealing plate of the third preferred embodiment;

FIG. 15 is a perspective view of a further intermediate in the process of fabricating the sealing plate of the third preferred embodiment;

FIG. 16 is a cross-sectional view of a still further intermediate in the process of fabricating the sealing plate of the third preferred embodiment;

FIG. 17 is a cross-sectional view of the sealing plate of the third preferred embodiment, FIGS. 16 and 17 showing the inversion of the sealing plate from the configuration obtained as the sealing plate is cut from the tubing shown on FIG. 10;

FIG. 18 is an exploded perspective view of the third preferred embodiment, and

FIG. 19 is a cross-sectional view of the third preferred embodiment.

DESCRIPTION OF THE PREFERRED EMBODIMENTS

Figure 6:
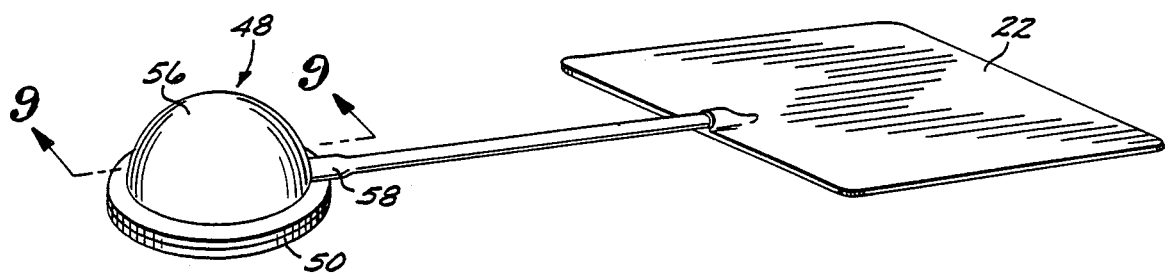
FIG. 6 is a perspective view of a second preferred embodiment of the injection reservoir of the present invention, the figure also showing a tissue expander bag to which the injection reservoir is fluidly connected.

The following specification, taken in conjunction with the drawings, sets forth the preferred embodiments of the present invention. The embodiments of the invention disclosed herein are the best modes contemplated by the inventors for carrying out their inventions in a commercial environment, although it should be understood that various modifications can be accomplished within the parameters of the present invention.

Referring now to FIGS. 1 through 5 of the appended drawings, a first preferred embodiment 20 of the injection button or reservoir of the present invention is disclosed. As it was noted in the introductory section of the present application for United States patent, the injection reservoir or button 20 of the present invention is used primarily in connection with a surgically implantable tissue expander, such as the tissue expander 22 shown on FIG. 1. A detailed description of a tissue expander and of its role in generating skin flaps (not shown) or enlargements (not shown), primarily for the purposes of plastic or reconstructive surgery, is found in U.S. Pat. No. 4,217,889, the specification of which is expressly incorporated herein by reference. It should be sufficient to note, for the purposes of explaining the present invention, that the injection reservoir or button 20 must be biocompatible for temporary implantation under the skin, and must be self-sealing to repeated punctures by a hypodermic needle and also capable of withstanding the hydrostatic pressure of the fluid within the expansion bag, whereby liquid can be either introduced or withdrawn from the tissue expander 22 through the injection reservoir 20. Instead of being used in conjunction with tissue expanders, the injection reservoir 20 of the present invention (as some other prior art injection reservoirs as well) can also be used in conjunction with certain drug delivery devices (not shown).

Referring now primarily to FIGS. 2 through 5 of the drawings, a base 24, an upper or top portion 26, and a bent sealing plate 28 are shown as important components of the first preferred embodiment 20 of the injection reservoir of the present invention.

The base 24 is substantially flat, and preferably comprises fabric reinforced bioimplantable silicone rubber. DACRON material is highly suitable to serve as the reinforcing fabric (not shown) of the base 24.

The upper or top portion 28 of the injection button 20 preferably has the configuration shown on FIGS. 1-5, i.e., it is preferably elongated, having a middle section 30 of substantially cylindrical curvature and two curvilinear end sections 32 and 34, which are surrounded by a substantially flat flange 36. The entire top portion 26 preferably comprises a single, unitary piece of biocompatible silicone rubber, which can be manufactured as such, for example, by molding or casting, with molding being preferred. The top portion 26 is attached to the base 24 through an intermediate sheet (not shown) of thin silicone rubber, which in the herein-described preferred embodiment is only approximately 0.010" (0.25 mm) thick. The thin sheet (not shown) is applied as raw silicone rubber, and is thereafter vulcanized to affix the top portion 26 to the base 24. Alternatively, the top portion 26 may be glued to the base 24 with a suitable glue (not shown) capable of bonding silicone rubber.

The base 24 and the top portion 26 of the injection reservoir 20 jointly define a chamber 38 into which liquid, such as saline solution (not shown) can be injected, and retained. Whereas the above-mentioned biological grade silicone rubber is a highly suitable and preferred material for the base 24 and the top portion 26, other biocompatible materials, such as certain latex, polycarbonate and polyurethanes are also suitable.

Referring now principally to FIGS. 2, 3 and 4, the sealing plate or sheet 28, which comprises a principal novel feature of the present invention, is shown. In accordance with the present invention, the sealing plate or sheet 28 is an elastic rubber sheet, which is originally flat, as is shown on FIG. 2, and is bent into a curvilinear configuration to become at least an inner wall of the chamber 38. In this regard, it is noted that the sealing plate 28 must comprise elastic material, and although preferably it is made of biocompatible silicone rubber, it does not need to be biocompatible unless it is exposed for contact with living tissue (not shown). The sheet 28 may be approximately 0.005 to 0.5 inch thick, although in the herein-described specific preferred embodiment, the sheet 28 is approximately 0.075 inch thick. FIGS. 2, 3 and 4 indicate that before the top portion 26 is affixed to the base 24, the sealing sheet 28 is inserted into the top portion 26 of the injection reservoir 20 to be affixed to the middle section 30 thereof.

Actually, in the herein-described specific embodiment, the bent sealing plate or sheet 28 is affixed to the interior wall of the middle section 30 through a thin silicone rubber sheet (not shown), which is applied as raw rubber and thereafter vulcanized to bond the sealing plate 28 and the middle section 30 together. Just like the thin sheet of rubber (not shown) which is utilized to bond the top portion 26 to the base 24, the thin sheet of rubber (not shown) used to bond the sealing plate 28 to the middle section 30 is also approximately 0.010" (0.25 mm) thick. Alternatively, the sealing plate 28 may also be glued to the middle section 30 with a suitable glue (not shown).

The sealing plate 28 is preferably manufactured by molding, although it can also be made by suitable casting techniques. As it should be already apparent from the foregoing description, the important feature of the sealing plate 28 is that it is made as a flat sheet (as shown on FIG. 2), and is thereafter incorporated in the injection button 20 in a bent configuration. Consequently, the inner portion of the sheet 28 is under compression, and renders the sheet 28 self-sealing to small punctures of the type which are caused by insertion of a hypodermic needle (not shown).

Referring still principally to FIGS. 2 through 5, a metal guard plate 40 is shown incorporated in the injection button 20. The guard plate 40 is configured to protect the base 24 and the two end portions 32 of the injection reservoir 20 from being punctured by an accidentally overextended hypodermic needle (not shown). To this end, preferably the guard plate 40 essentially conforms to the shape of the injection button 20, and includes a flat elongated base plate 42 and two side plates 44. The side plates 44 are optional, in that the entire guard plate 40 may also be flat so as to have the configuration of the flat base 42.

The herein-described first specific embodiment 20 of the injection button or reservoir of the present invention is assembled by placed the guard plate 40 within the interior and by applying the thin raw silicone rubber sheets (not shown) between the interior of the middle section 30 and the bent sealing plate 28, and between the top portion 26 and the base 24, respectively. Thereafter, the assembly is subjected to vulcanizing conditions (approximately 300 Fahrenheit and a pressure of approximately 10 to 20 PSI) to vulcanize the thin raw silicone rubber sheets (not shown) and bond the assembly together. A tube or conduit 46 integrally molded with the top portion 26 connects the injection reservoir 20 with the inflatable bag 22 of the tissue expander.

Referring now to FIGS. 6 through 9 of the appended drawings, a second preferred embodiment 48 of the injection button or reservoir of the present invention is disclosed. Important components of the second preferred embodiment are a base 50, a guard plate 52, and a substantially dome-shaped member 54 which acts as a sealing plate. The dome-shaped member 54 comprises elastic rubber material and is self-sealing to punctures by hypodermic needles (not shown) by virtue of having been inverted from the original configuration in which the dome-shaped member 54 was made. As in the case of the sealing plate 28 of the first preferred embodiment 20, the dome-shaped sealing plate 54 of the second embodiment is also preferably manufactured by molding.

Figure 8:
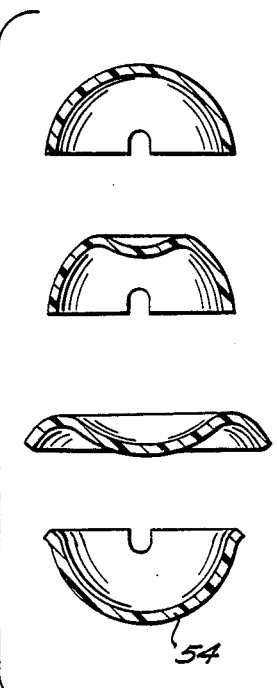
FIG. 8 includes a series of schematic cross-sectional views showing a molded, substantially dome-shaped member being inverted for the purpose a self-sealing wall of the second preferred embodiment of the injection reservoir of the present invention.

FIG. 8 indicates schematically the inversion of the originally manufactured, preferably molded, dome-shaped member to provide the sealing plate 54 which has its interior (concave) side in compression so that it is self-sealing to small punctures. The range of the wall thickness of the dome-shaped sealing plate 54 is approximately 0.005 to 0.5 inch; in the herein-described second preferred embodiment, the dome-shaped sealing plate 54 is approximately 0.075 inch thick.

Figure 7:
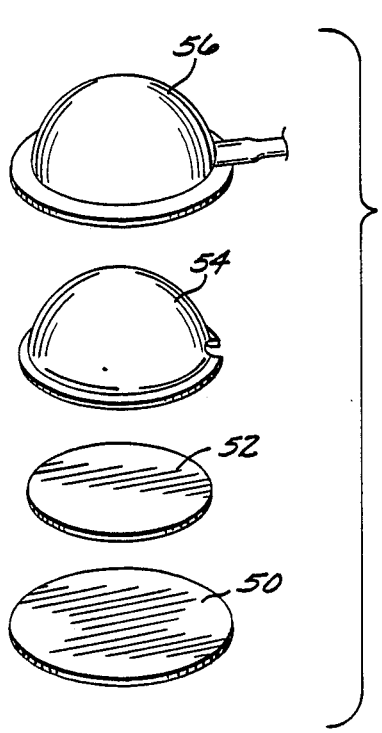
FIG. 7 is an exploded perspective view of the second preferred embodiment of the injection reservoir of the present invention.
Figure 9:
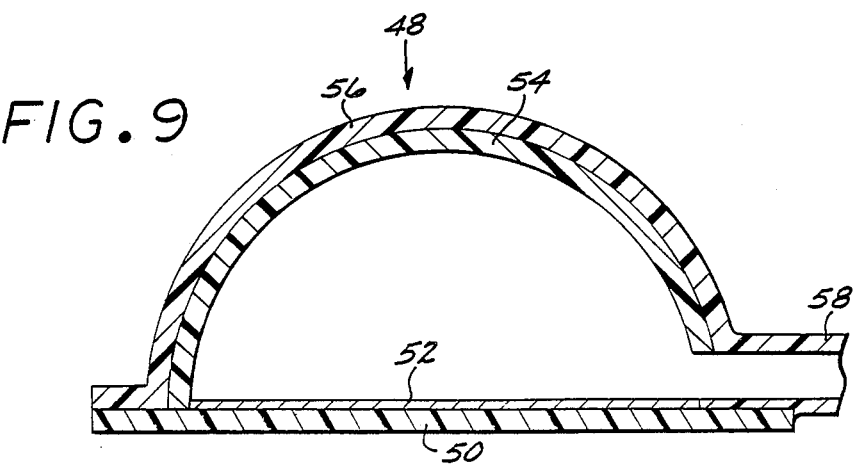
FIG. 9 is a cross-sectional view of the second preferred embodiment of the injection reservoir of the present invention, the cross-section being taken on lines 9,9 of FIG. 6.

Preferably, as is shown on FIGS. 7 and 9 of the appended drawings in connection with the second preferred embodiment 48, the dome-shaped sealing plate 54 comprises an interior wall of the injection reservoir 48, and is affixed to an exterior, dome-shaped wall 56 with a suitable adhesive. All components of the second preferred embodiment 48 of the injection reservoir which come into contact with living tissue (not shown) must be made of biocompatible material to permit implantation. As it is discussed above in connection with the first preferred embodiment 20, medical grade silicone rubber is highly suitable for this purpose, although other materials are also suitable. The dome-shaped sealing plate must be made of an elastic rubber, although if it is contained entirely within the interior of the injection reservoir 54, it need not be made of a biocompatible material. Nevertheless, medical grade silicone rubber is highly suitable, and is the preferred material for the dome-shaped sealing plate 54 as well.

The exterior dome-shaped wall 56 of the injection reservoir, into which the interior sealing plate 54 is affixed by gluing or the like, is attached to the base 50 with a suitable adhesive (not shown), although a thin sheet (not shown) of vulcanizable silicone rubber can also be used for this purpose. The guard plate 52, which is contained in the interior of the injection reservoir 48, protects the base 50 from accidental puncture by a hypodermic needle (not shown). A tube 58, which may be integrally molded with the external wall 56, or may be affixed thereto by gluing, connects the injection button 48 with the inflatable bag 22 of the tissue expander. The injection reservoir may also be mounted directly to the inflatable bag with openings being placed in the guard plate 52 and in the base 50 for fluid passage. The second preferred embodiment 48 of the injection button or reservoir of the present invention, just like the first preferred embodiment 20, can be used not only in conjunction with tissue expanders, but also in conjunction with bioimplantable drug delivery and like devices.

Referring now to FIGS. 10 through 19 of the appended drawings, a third preferred embodiment 60 of the injection reservoir of the present invention is disclosed. In this preferred embodiment, as well as in the herein-above described two embodiments, a resilient sealing member 62 is kept in a configuration where its side abutting the interior of the injection reservoir is in structural compression, whereby the sealing member 62 is self-sealing to punctures by a hypodermic needle (not shown).

The sealing member 62 of the third preferred embodiment is fabricated from a hollow cylinder or tube 64, shown on FIG. 10, which is made of a resilient elastic material, preferably silicone rubber. The tube 64 has a diameter of approximately 0.2 to 1.00", and a wall thickness of approximately 0.010 to 0.5". Preferably, as in the herein-described third specific embodiment 62, the tube 64 has a 0.375" diameter and a wall thickness of 0.025". A slot or cut 66 is placed into the tube 64 substantially parallel with its longitudinal axis, as is shown on FIG. 11. Thereafter, the slotted tube 68 is unfolded to provide a rectangular piece 70, and the sealing member 62 is die-cut from the rectangular piece 70. FIGS. 12 and 13 show the natural tendency of the rectangular piece 70 to curl into its original tubular configuration.

It should be apparent from the foregoing that distortion or flattening of the disc-shaped sealing member 62 from its "natural" tubular configuration causes compression in the exterior convex wall 72 of the disc. In order to obtain optimal self-sealing capability, the disc-shaped sealing member is inverted, as is shown on FIGS. 16 and 17. In other words, the naturally convex wall 72 of the tube 64 becomes the interior wall of the sealing member 62 which abuts the interior of the injection reservoir 60.

Structural components and construction of the third preferred embodiment 60 of the injection reservoir are shown on FIGS. 18 and 19. Thus, the injection reservoir 60 includes a biocompatible silicone rubber base 74, a substantially flat metal guard plate 76, a metal guard cylinder 78, the inverted sealing member or disc 62 and a biocompatible silicone rubber outer housing 80. The guard cylinder 78 includes an aperture 82 which permits fluid communication from the interior of the injection reservoir 60 to an expansion bag 22 through a tubing 46. The inverted sealing disc 62 is placed on top of the metal guard cylinder 78, as is best shown in the cross-sectional view of FIG. 19. The outer housing 80 has a flange 84 which is affixed to the base 74 either through a thin sheet of silicone rubber (not shown) in a vulcanization step, or by gluing. The herein-described third specific embodiment 60 of the injection reservoir is approximately 0.600" in diameter, and approximately 0.25" high.

Inasmuch as several modifications of the herein-described injection button or reservoir may become readily apparent to those skilled in the art in light of the above disclosure, the scope of the present invention should be interpreted solely from the following claims as such claims are read in light of the disclosure.

What is claimed is:

1. A self-sealing injection reservoir adapted to be punctured by a hypodermic needle, the reservoir comprising:
   a body defining a chamber for holding liquid, said body including a base;
   a substantially dome-shaped member made of elastic material and having a concave interior side which is under compression as a result of having been manufactured into a substantially dome-shaped configuration and thereafter inverted, the dome shaped member comprising at least an interior wall of the chamber and being disposed in a locaion of the chamber which is adapted to be punctured by the hypodermic needle;
   duct means for conducting liquid out of the chamber, and
   guard means incorporated in the chamber for preventing accidental puncture of the base with the hypodermic needle.

2. The self-sealing injection reservoir of claim 1 wherein the chamber has a substantially dome-shaped exterior wall, and wherein the inverted dome-shaped member is affixed to the exterior wall within the interior of the chamber.

3. The self-sealing injection reservoir of claim 1 wherein the inverted dome-shaped member comprises silicone rubber.

4. The self-sealing injection reservoir of claim 2 wherein the base is substantially flat, and wherein the exterior wall is affixed to the base by gluing.

5. A self-sealing injection reservoir adapted to be surgically placed under the skin of humans or domestic animals for the purpose of having liquids injected into the reservoir through the skin with a hypodermic needle, the reservoir comprising
   a base;
   a substantially dome shaped exterior wall affixed to the base, the base and the exterior wall jointly comprising a reservoir chamber for liquid;
   a substantially dome-shaped member made of elastic material comprising a body having its initially interior walls turned outside, and its initially exterior walls turned inside, said member having been made by a process of forming elastic material into a substantially dome-shaped configuration and thereafter inverting the dome-shaped configuration whereby the concave interior side of the dome-shaped member is under compression, the dome shaped member being affixed to the exterior wall within the interior of the chamber;
   duct means in fluid communication with the reservoir chamber for permitting flow of liquid out of the reservoir chamber or into the reservoir chamber, and
   guard means for guarding the base against being punctured by the hypodermic needle.

6. The self-sealing injection reservoir of claim 5 wherein the base is substantially flat.

7. The self-sealing injection reservoir of claim 6 wherein the inverted dome-shaped member is affixed to the exterior wall by gluing.

8. The self-sealing injection reservoir of claim 5 wherein the inverted dome-shaped member is made of silicone rubber.

9. The self-sealing injection reservoir of claim 5 wherein the guard means comprise a metal plate disposed within the interior of the chamber.

* * * * *